US012268383B2

(12) United States Patent
Bowers (10) Patent No.: US 12,268,383 B2
(45) Date of Patent: Apr. 8, 2025

(54) SURGICAL SUTURE MANAGEMENT

(71) Applicant: Mayo Foundation for Medical Education and Research, Rochester, MN (US)

(72) Inventor: Steven Bowers, Ponte Verde Beach, FL (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 502 days.

(21) Appl. No.: 17/599,131

(22) PCT Filed: Apr. 14, 2020

(86) PCT No.: PCT/US2020/028043
§ 371 (c)(1),
(2) Date: Sep. 28, 2021

(87) PCT Pub. No.: WO2020/214548
PCT Pub. Date: Oct. 22, 2020

(65) Prior Publication Data
US 2022/0151607 A1    May 19, 2022

Related U.S. Application Data

(60) Provisional application No. 62/834,277, filed on Apr. 15, 2019.

(51) Int. Cl.
*A61B 17/06* (2006.01)
*A61B 17/30* (2006.01)
(Continued)

(52) U.S. Cl.
CPC .............. *A61B 17/06061* (2013.01); *A61B 17/06166* (2013.01); *A61B 17/30* (2013.01);
(Continued)

(58) Field of Classification Search
CPC ........ A61B 17/06061; A61B 17/06166; A61B 17/30; A61B 34/30; A61B 90/92;
(Continued)

(56) References Cited

U.S. PATENT DOCUMENTS

| 3,695,271 A | 10/1972 | Chodorow |
| 5,207,703 A | 5/1993 | Jain |
| 6,398,557 B1 * | 6/2002 | Hoballah ............... G09B 23/28 434/262 |

(Continued)

OTHER PUBLICATIONS

PCT International Preliminary Report on Patentability in International Appln. No. PCT/US2020/028043, dated Sep. 28, 2021, 7 pages.

(Continued)

*Primary Examiner* — Sarah A Long
*Assistant Examiner* — James R McGinnity
(74) *Attorney, Agent, or Firm* — Fish & Richardson P.C.

(57) ABSTRACT

A suture-carrying apparatus includes a suture engaging ridge for placement and retention of surgical sutures, and a base for conveniently mounting the apparatus to a predetermined location, such as a body structure, which is reachable by robotic arms during a robot-assisted surgical operation. The base may be configured to allow stability of the apparatus for one-handed placement and retrieval of sutures from the ridges.

11 Claims, 9 Drawing Sheets

(51) Int. Cl.
*A61B 34/30* (2016.01)
*A61B 90/92* (2016.01)

(52) U.S. Cl.
CPC .............. *A61B 34/30* (2016.02); *A61B 90/92* (2016.02); *A61B 2017/0618* (2013.01); *A61B 2017/306* (2013.01)

(58) Field of Classification Search
CPC ...... A61B 2017/0618; A61B 2017/306; A61B 17/0483; A61B 2017/0482
See application file for complete search history.

(56) References Cited

U.S. PATENT DOCUMENTS

| | | | |
|---|---|---|---|
| 2009/0005794 A1* | 1/2009 | Lowry | A61B 17/06061 606/148 |
| 2010/0056858 A1* | 3/2010 | Mokelke | A61B 17/3207 607/10 |
| 2010/0274091 A1* | 10/2010 | Rothstein | A61B 17/3423 606/228 |
| 2014/0039527 A1 | 2/2014 | Avelar et al. | |
| 2016/0030036 A1 | 2/2016 | Belman et al. | |
| 2018/0070938 A1 | 3/2018 | Sauer | |

OTHER PUBLICATIONS

PCT International Search Report and Written Opinion in International Appln. No. PCT/US2020/028043, dated Jul. 16, 2020, 9 pages.

\* cited by examiner

SURGICAL SUTURE MANAGEMENT

CROSS-REFERENCE TO RELATED APPLICATIONS

This application is a National Stage application under 35 U.S.C. § 371 of International Application No. PCT/US2020/028043, having an International Filing Date of Apr. 14, 2020, which claims the benefit of U.S. Provisional Application Ser. No. 62/834,277, filed Apr. 15, 2019. The disclosure of the prior applications are is considered part of (and are incorporated by reference in) the disclosure of this application.

TECHNICAL FIELD

This document describes devices, systems, and methods related to management of surgical sutures in a surgical operation.

BACKGROUND

Robot-assisted surgery is widespread and no longer limited to particular types of surgeries, such as urology use. Robot-assisted procedures are now used in many general and bariatric surgeries. An increasing number of surgeons use robot technologies for many abdominal procedures.

With robot-assisted surgery, sutured fixation may provide clinical advantages over other mechanical fixation techniques for various operations such as gastrointestinal connections and for hernia mesh. Established practice typically involves a human assistant (e.g., a nurse) who passes and retrieves sutures to the robotic arms in between steps of robotic operations. Such manual practice is inefficient in terms of time and manpower, and exposes the patient to a lost suture in the abdomen and/or to additional cutting for the assistant trocar port.

SUMMARY

Some embodiments described herein include systems, devices, apparatuses, methods, and other techniques for managing surgical sutures in a robot-assisted surgical operation. In some examples, a suture management apparatus (also referred to as a suture-carrying apparatus) includes a suture engaging ridge for placement and retention of surgical sutures, and a base for conveniently mounting the apparatus to a predetermined location, such as a body structure, which is reachable by robotic arms during a robot-assisted surgical operation. The base may be configured to allow stability of the apparatus for one-handed placement and retrieval of sutures from the ridges. In some implementations, the base may be configured to provide a modest suction cup effect when placed on a body structure (e.g., a liver in an abdominal cavity). The apparatus may be made of one or more flexible materials with identical or different flexibilities (e.g., elasticities). For example, the ridge may be made of flexible material with a first flexibility, and the base may be made of flexible material with a second flexibility different than the first flexibility. In some implementations, the ridge may be made of firmer silicon than the silicon of which the base may be made.

In some implementations, a suture-carrying apparatus that engages one or more surgical sutures can be inserted into a body cavity defined with a human body. One or more surgical instruments (e.g., grasping devices) attached to the robot arm assemblies can pick up the apparatus and insert it into the body cavity through a body opening or a tool (e.g., a trocar or a sleeve) engaged with the body opening. The apparatus may be placed on a desired area within the cavity, such as an organ surface (e.g., a liver surface), adjacent to a body portion (e.g., gastrointestinal organ) that needs to be stitched. The apparatus may be attached to the area by a suction cup effect created by the base of the apparatus and/or a surface tension between the area and the base of the apparatus. Once the apparatus is placed in the body cavity, a surgical suture is removed from engagement with the apparatus and used to stitch a target organ. In some embodiments, a grasping device of one of the robot arm assemblies may grasp the surgical suture and retrieve it from the apparatus, while another grasping device of another of the robot arm assemblies grasps a portion of the apparatus (e.g., the ridge or the base of the apparatus) to hold the apparatus to remain attached onto the mounting area. Once the intended procedure (e.g., stitching) has been completed, the grasping devices of the robot arm assemblies can return the surgical suture and engage it with the apparatus again for storage.

Particular embodiments described herein include an apparatus for managing surgical sutures in a robot-assisted surgical operation. The apparatus may include an elongate ridge configured to removably engage one or more surgical sutures, and a flexible base configured to removably mount the elongate ridge to a body structure. The flexible base may include one or more flexible wings attached to a bottom of the ridge and at least partially extending around the ridge. The apparatus may be reconfigurable between: (i) a low-profile arrangement in which the one or more flexible wings are contracted toward the elongate ridge such that the apparatus can be passed through a trocar or body incision and (ii) an expanded arrangement in which the flexible wings are extended away from the elongate ridge In some implementations, the system can optionally include one or more of the following features. The ridge may include one or more edges at the bottom. The one or more flexible wings may be connected to the one or more edges. The one or more flexible wings may include a plurality of wings interconnected to one another. The plurality of wings may form a suction cup. The one or more flexible wings may be configured to be flaccid relative to the elongate ridge. The body structure may include an organ.

Particular embodiments described herein include a method for managing surgical sutures in a robot-assisted surgical operation. The method may include inserting a suture-carrying apparatus through a trocar engaged with a human body and into a body cavity defined with the human body. Multiple surgical sutures may be engaged with the suture-carrying apparatus during the inserting. While the suture-carrying apparatus may be within the body cavity, the method may further include removing a first surgical suture of the multiple surgical sutures from engagement with the suture-carrying apparatus. The removing may be performed using a grasping device of a robotic surgery system.

In some implementations, the system can optionally include one or more of the following features. The suture-carrying apparatus may include an elongate ridge configured to removably engage one or more surgical sutures; and a flexible base configured to removably mount the elongate ridge to a body structure. The flexible base may include one or more flexible wings extending from a bottom of the ridge and at least partially around the ridge. The method may further include placing the suture-carrying apparatus on an organ to enable the flexible base to attach to the organ with suction pressure created by the flexible wings. The method may further include, prior to inserting, deforming the apparatus to a low-profile arrangement in which the one or more flexible wings are contracted toward the elongate ridge such that the apparatus can be passed through the trocar. The method may further include, after inserting, reconfiguring the apparatus from the low-profile arrangement to an expanded arrangement in which the one or more flexible wings are extended away from the elongate ridge.

The devices, system, and techniques described herein may provide one or more of the following advantages. First, some embodiments described herein include a suture management apparatus which has a simple design and made of inexpensive materials, and which enables entry and retrieval of multiple surgical sutures in a safe manner during a robot-assisted operation. The apparatus is configured to enable suture passing, retrieval, and intraoperative suture management in a body cavity (e.g., an abdominal cavity) without manual intervention during robot-assisted operations. The apparatus improves typical practice where an assistant (e.g., nurse), away from the surgeon sitting at a surgeon-side subsystem, passes surgical sutures to, retrieve them from, robot arm assemblies between steps of a robot-assisted operation. For example, the apparatus may eliminate human error or miscommunication in selecting desired sutures and engaging them with, and removing them from, robotic arm assemblies. The apparatus enables sparing time and manpower of an assistant who would otherwise pay attention to proper selection, engagement and retrieval of surgical sutures.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1A:
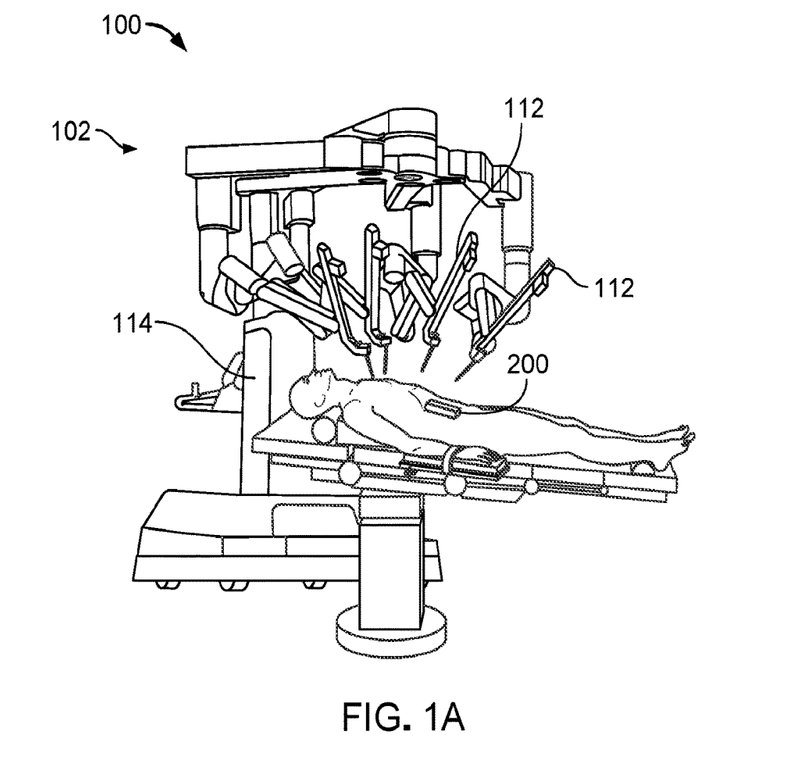
FIG. 1A illustrates an example patient-side subsystem of an example robot-assisted surgical system.
Figure 1B:
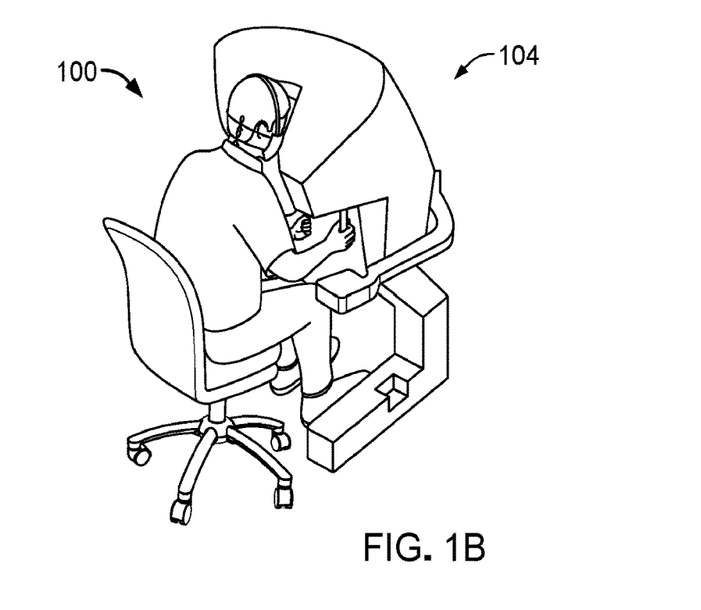
FIG. 1B illustrates an example surgeon-side subsystem of the robot-assisted surgical system.

Referring to FIGS. 1A and 1B, an example robot-assisted surgical system 100 is described. The system 100 may include a patient-side subsystem 102 and a surgeon-side subsystem 104. The surgeon-side subsystem 104 may be remotely connected to the patient-side subsystem 102 and used by a surgeon to manipulate surgical instrument movements on the patient-side subsystem 102. The system 100 includes robotically manipulated surgical instruments that can be inserted through small surgical apertures to treat tissues at surgical sites within the patient. The system 100 may enable the surgeon to remotely manipulate working ends of the surgical instruments to perform intricate surgical tasks. For example, the surgeon sitting on the surgeon-side subsystem 104 can control the surgical instruments on the patient-side subsystem 102 to pivot shafts of the instruments at a small surgical aperture, slide the shafts through the aperture, rotate the shaft within the aperture, and perform other suitable procedures.

The patient-side subsystem 102 may include one or more robotic arm assemblies 112, each pivotally coupled to a system base 114. In some implementations, one or two of the robotic arm assemblies 112 may engage surgical instruments at their working ends, and at least one of the robotic arm assemblies 112 may engage a stereo endoscope. Other surgical instruments, endoscopes, and/or devices, such as an image capturing device, an ultrasound transducer, can be engaged with the robotic arm assemblies for various functions during operations. Each robotic arm assembly 112 may include a setup arm configured to hold and position a surgical instrument so that a pivot point occurs at its entry aperture into the patient. The robotic arm assembly 112 may further include a device configured to manipulate its held device so that the held device is pivoted around the pivot point, inserted into and retracted out of the entry aperture, and rotated about its shaft axis.

The surgeon-side subsystem 104 may be configured as a console that includes a display device that displays the surgical work site in stereo vision from images captured by the stereoscopic camera of the patient-side subsystem 102. The surgeon-side subsystem 104 includes eyepieces in the display device so that the surgeon can view a display screen (e.g., left and right display screens) inside the display device. While viewing an image of the surgical work site on the display device, the surgeon performs the surgical procedures on the patient by manipulating one or more control input devices, which control the motion of robotic instruments engaged with the robotic arm assemblies 112. Examples of the control input devices include hand controllers with multiple degrees of freedom (e.g., six degrees of freedom), foot pedals, and other suitable controllers. The surgeon-side subsystem 104 may include a processor for performing various functions in the medical robotic system. One example function is to translate and transfer the mechanical motion of input devices to actuate their respective joints in their associated robotic arm assemblies 112 so that the surgeon can effectively manipulate the surgical instruments.

The system 100 may further include a suture-carrying apparatus 200 for carrying surgical sutures to be used in robot-assisted operations. The suture-carrying apparatus 200 is configured to carry one or more surgical sutures and may be conveniently inserted and placed into a body cavity (e.g., abdominal cavity) so that the surgeon at the surgeon-side subsystem 104 manipulates the robotic instruments (e.g., needle holders or other grasping devices) arranged at the working ends of the robotic arm assemblies 112 to retrieve desired surgical sutures from the apparatus 200 when needed, and place them back to the apparatus 200 once the necessary steps (e.g., stitching) have been performed. An example of the suture-carrying apparatus 200 is illustrated and described in further detail herein, for example with reference to FIGS. 2A, 2B, 3A, and 3C.

Figure 2A:
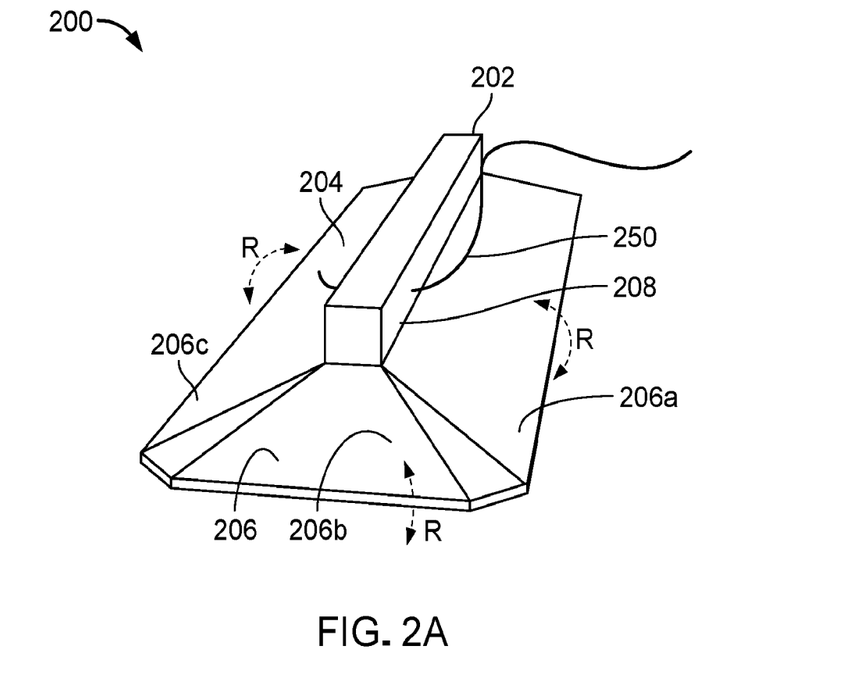
FIG. 2A is a schematic top perspective view of an example suture-carrying apparatus.
Figure 2B:
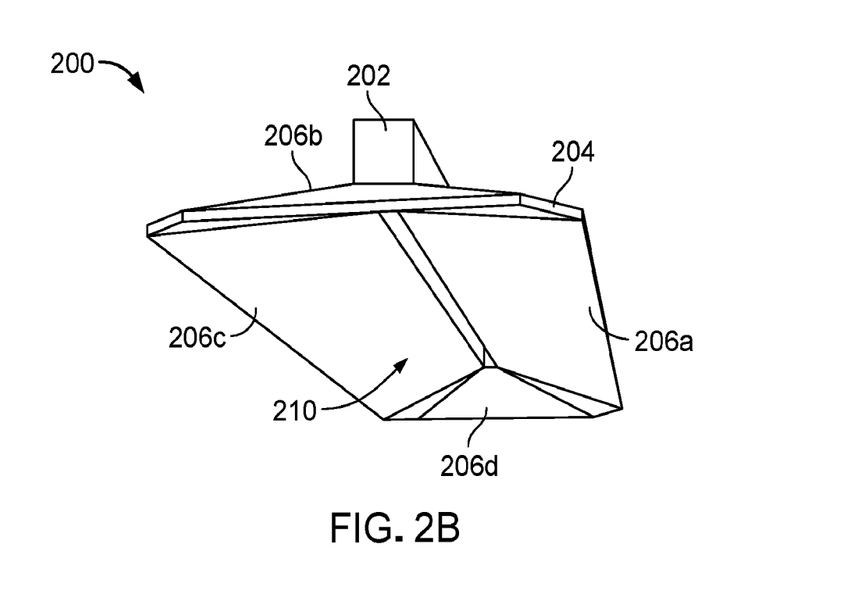
FIG. 2B is a schematic bottom perspective view of the suture-carrying apparatus of FIG. 2A.
Figure 3A:
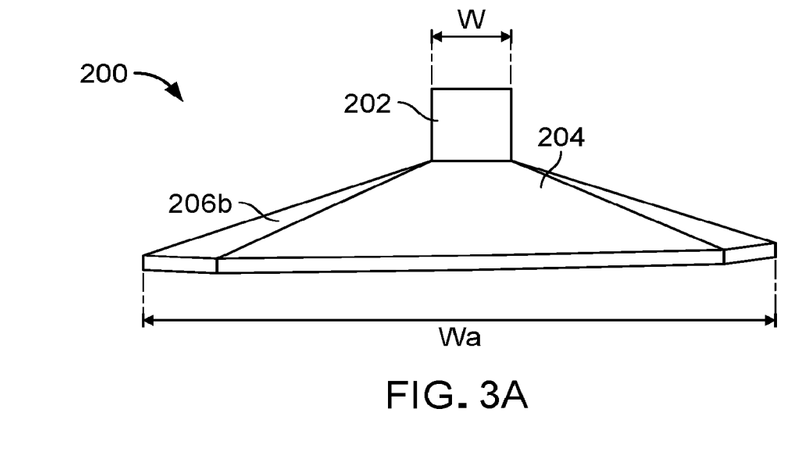
FIG. 3A is a schematic front view of the suture-carrying apparatus of FIG. 2A.
Figure 3B:
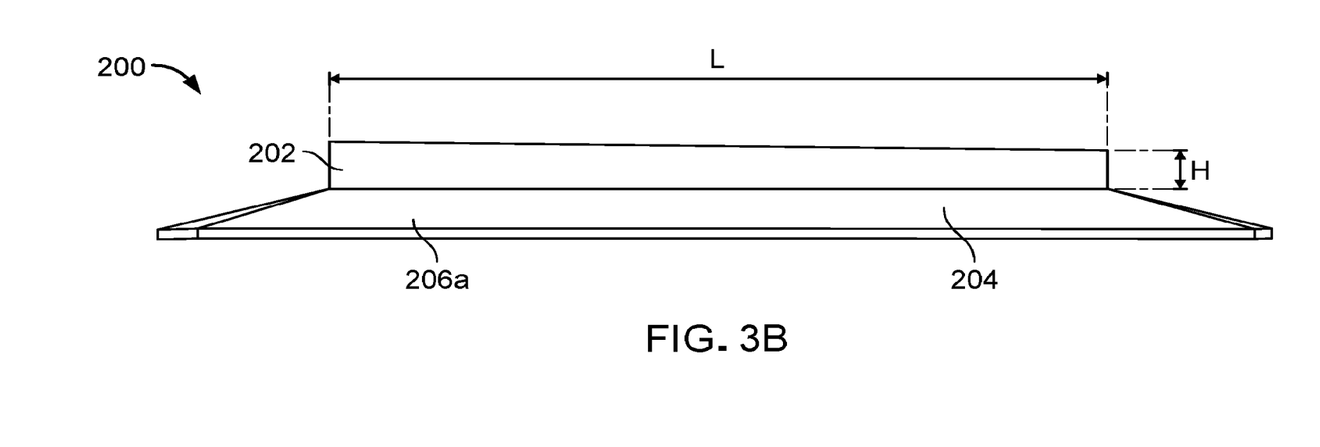
FIG. 3B is a schematic side view of the suture-carrying apparatus of FIG. 2A.

Referring to FIGS. 2A, 2B, 3A, and 3B, an example of the suture-carrying apparatus 200 is described. The suture-carrying apparatus 200 is configured to carry and manage surgical sutures in robot-assisted surgical operations and may include a ridge 202 and a base 204. The ridge 202 may be formed as an elongate body (e.g., block, tube, cylinder, or other shapes) configured to removably engage and retain one or more surgical sutures 250. For example, as illustrated in FIGS. 3A and 3B, the ridge 202 has a length (L) greater than a width (W) and a height (H). The ridge 202 can be made of one or more flexible materials, such as silicon, and permit the surgical sutures to pierce and remain engaged with the ridge 202. In some implementations, the ridge 202 includes opposite side surfaces 208 longitudinally extending along the length (L) of the ridge 202. As illustrated in FIG. 2A, surgical sutures 250 can pass through the opposite side surfaces 208 of the ridge 202 and engage with the ridge 202 for storage.

The base 204 is configured to removably mount the apparatus 200 to a body structure, such as on a body skin or within a body cavity. The base 204 may be made of one or more flexible materials, such as silicon. In some implementations, the base 204 may include one or more flexible wings 206 that are attached to a bottom of the ridge 202. The wings 206 may be connected to the bottom of the ridge 202 and arranged at least partially around the ridge 202. In embodiments where the ridge 202 includes four edges at the bottom, the base 204 may include four wings 206 (including 206a, 206b, 206c, and 206d) connected at the edges of the bottom of the ridge 202, respectively. In some embodiments, the base 204 includes the same number of wings 206 as the number of bottom edges of the ridge 202. In other embodiments, the base 202 includes more or less number of wings 206 than the number of bottom edges of the ridge 202. In yet other embodiments, the wings 206 may be configured as a single integral piece that is attached to the bottom of the ridge 202 such that the wings 206 spreads out from the bottom of the ridge 202. In some embodiments, the wings 206 may extend away from the ridge 202 and downwardly from the bottom of the ridge 202. In some embodiments, the wings 206 may be interconnected to one another (or formed as a single integral piece) around the ridge 202, thereby forming a recessed portion 210 (also referred to as a suction cup). The recessed portion 210 of the base 204 can create a suction cup effect when the base 204 is mounted to a surface of a body portion, such a body skin or an organ surface.

The wings 206 may be made of one or more flexible materials, such as silicon, and configured to flap (e.g., be limp or flaccid) relative to the ridge 202. As the wings 206 are flexible, the base 204 can deform in various configurations and result in a smaller profile of the apparatus 100. In one example, as indicated by arrows (R) in FIG. 2A, the wings 206a and 206c that are connected to the length (L) of the ridge 202 can flap/flex up toward the ridge 202 or flap/flex down away from the ridge 202, while the wings 206b and 206d that are connected to the width (W) of the ridge 202 can flex inwards or outwards, thereby reducing an entire width (Wa) of the apparatus 200. In another example, at least one of the wings 206 can roll inwards or outwards (along either direction of the arrows (R)), thereby reducing the entire width (Wa) of the apparatus 200.

In some embodiments, the apparatus 200 may be at least partially color-coded to distinguish different types and/or sizes of surgical sutures retained at the apparatus 200. For example, the ridge 202 have a plurality of sections with different colors or marks to indicate different types and/or sizes of surgical sutures being retained respectively.

Figure 4:
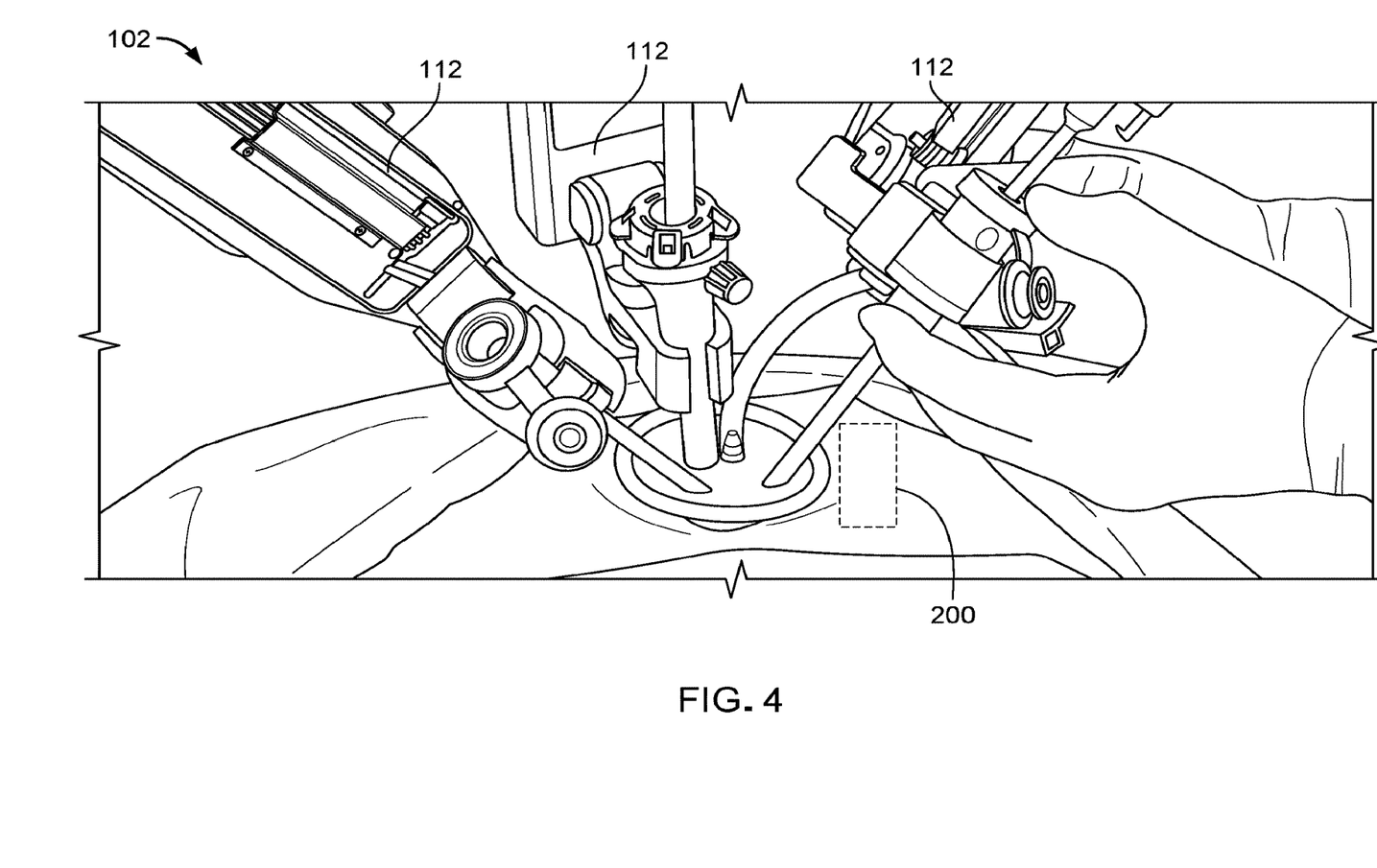
FIG. 4 illustrates an example placement of a suture-carrying apparatus with an example robot-assisted surgical system.

Referring also to FIG. 4, the suture-carrying apparatus 200 can be placed in one or more areas that the robotic instruments (e.g., needle holders) arranged at the working ends of the robotic arm assemblies 112 can conveniently reach to access surgical sutures from the apparatus 200. For example, the suture-carrying apparatus 200 can be placed at or adjacent to the surgical work site to reduce or minimize the movements of the robotic arm assemblies 112 to access the surgical sutures engaged with the apparatus 200. In some example implementations, the apparatus 200 may be inserted into and placed within the body cavity where a surgical operation is performed. The apparatus 200 may be removably attached to, or abutted against, an organ surface, such as a liver or other tissue(s), when the operation is performed on internal organs, such as gastrointestinal surgery. In other example implementations, the apparatus 200 may be removably attached to a body skin adjacent a body hole (e.g., made by a trocar), such as an abdomen as illustrated in FIG. 4. Other body portions, skins, and internal organs are also available for mounting/receiving the apparatus 200 during robot-assisted surgical operations.

In some implementations, the apparatus 200 has flexible wings 206 forming a suction cup (e.g., the recessed portion 210) at the bottom of the base 204. The apparatus 200 may be mounted to a body or organ surface by gently pushing the base 204 against the surface, which generates a suction cup effect between the base 204 and the surface. Alternatively or in addition, the apparatus 200 may be placed on a surface by natural force, such as gravity and/or surface tension. In other embodiments, one or more fasteners (e.g., sutures) may be used to mount the apparatus 200 to a desired body or organ area.

Figure 5:
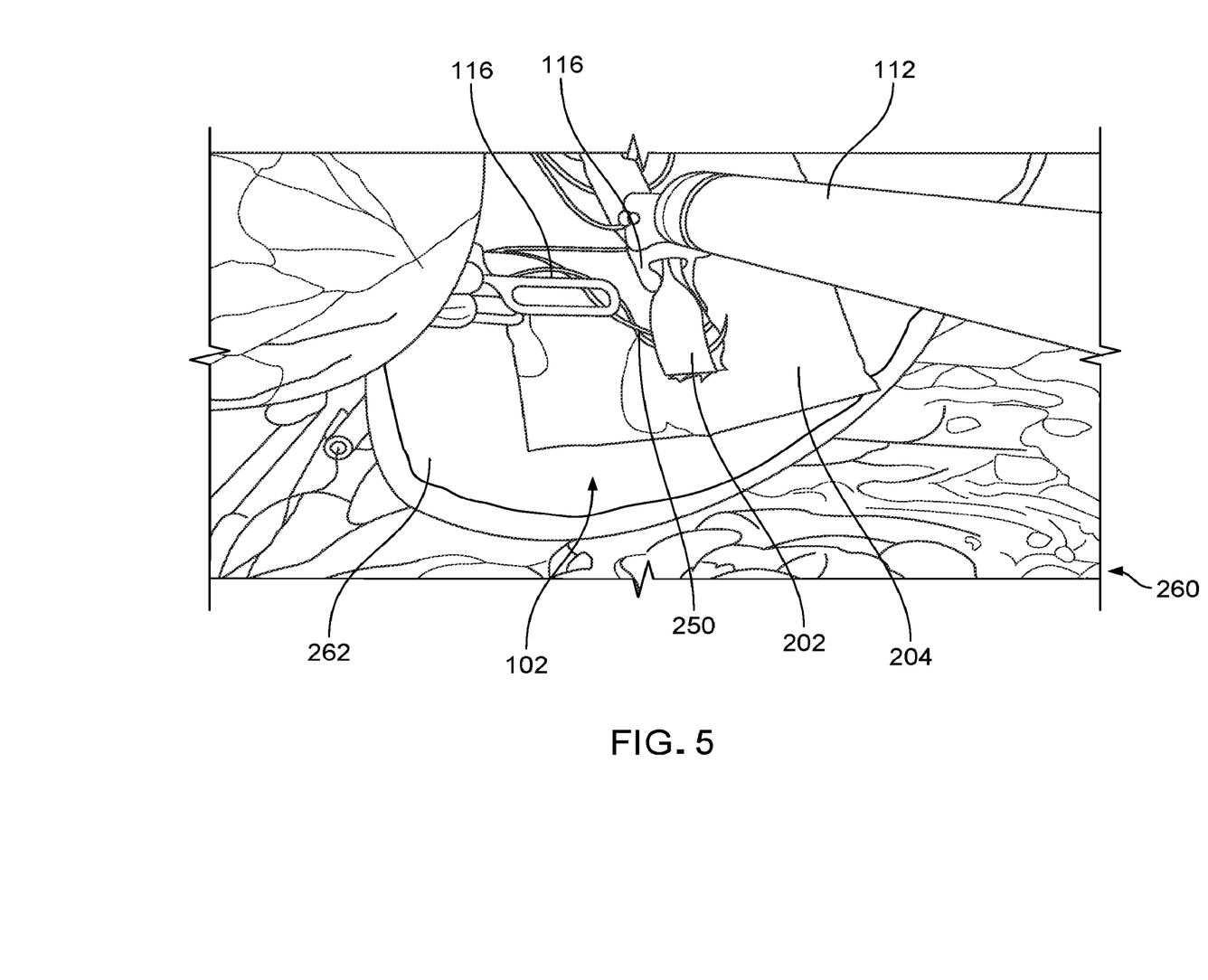
FIG. 5 illustrates an example body cavity that receives and provides an area onto which a suture-carrying apparatus is mounted.

FIG. 5 illustrates an example body cavity 260 within which a robot-assisted surgical procedure is being performed. Within the body cavity (which may be expanded by insufflation), various tissue surfaces are made accessible that can receive and provide an area 262 onto which the suture-carrying apparatus 200 is mounted. In some embodiments, the suture-carrying apparatus 200 that engages one or more surgical sutures 250 may be inserted into the body cavity 260, and reside within the body cavity 260 during a surgery. For example, a surgeon on the surgeon-side subsystem 104 (FIG. 1B) can control the robot arm assemblies 112 to grasp the apparatus 200 using a grasping device 116 connected to one of the robot arm assemblies 112, and insert it into the body cavity 260 through a body opening or a tool (e.g., a trocar or a sleeve) engaged with the body opening. While grasping the apparatus 200 using the grasping device 116, the robot arm assemblies 112 may be further controlled to move and place the apparatus 200 on a desired place 262 in the body cavity 260. Such a desired place 262 may be located adjacent to a body portion that needs to be stitched. Examples of such a desired place 262 include an organ surface, such as a liver. The apparatus 200 may be attached to the place 262 by a suction cup effect created by the base 204 of the apparatus 200 and/or a surface tension between the place 262 and the base 204 of the apparatus 200.

Once the apparatus 200 is placed in the body cavity 260, a surgical suture 250 is removed from engagement with the apparatus 200 and used to stitch a target organ. In some embodiments, a grasping device 116 of a robot arm assembly 112 may be used to grasp the surgical suture 250 and retrieve it from the ridge 202 of the apparatus 200, while another grasping device 116 of another robot arm assembly 112 grasps a portion of the apparatus 200, such as the ridge 202 or the base 204 of the apparatus 200, to hold the apparatus 200 to remain attached onto the place 262. Once the intended procedure (e.g., stitching) has been completed, the grasping devices 116 of the robot arm assemblies 112 can return the surgical suture 250 and engage it with the ridge 202 of the apparatus 200 again for storage.

Figure 6:
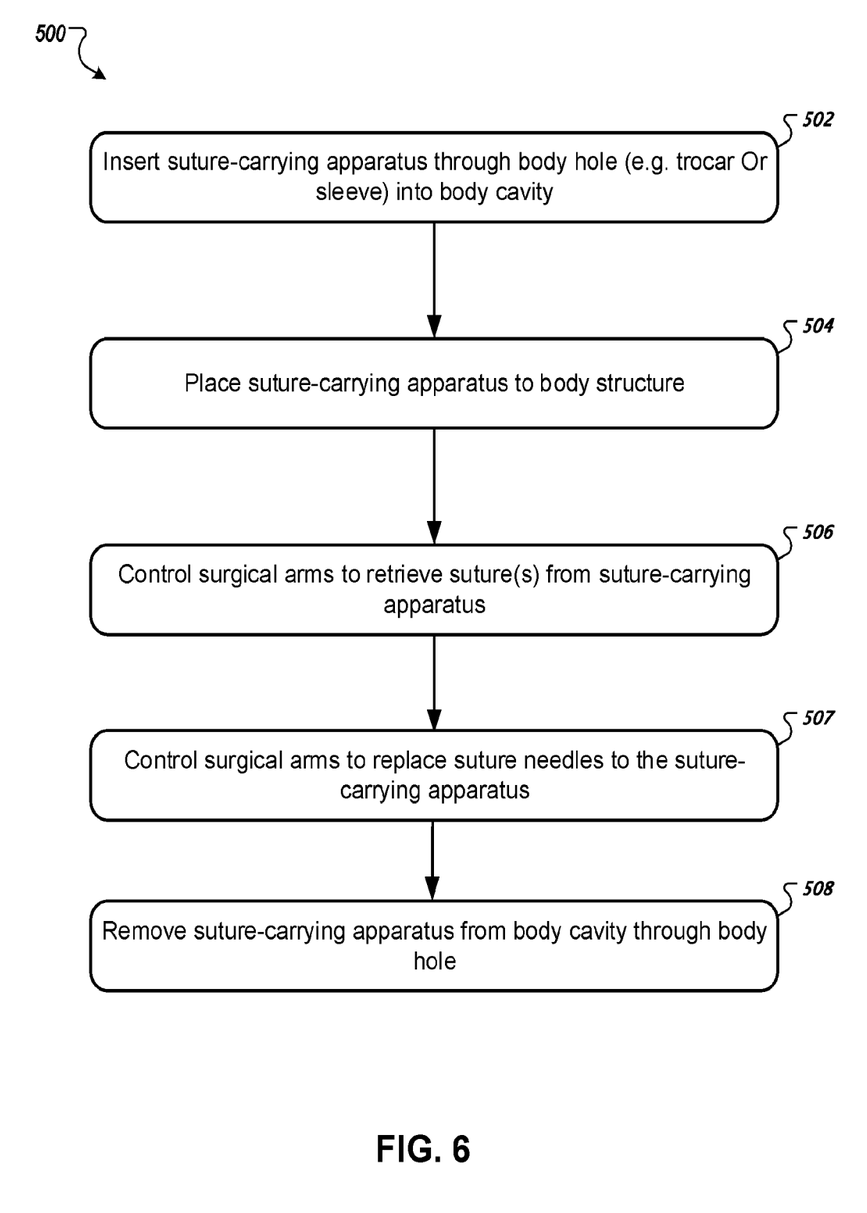
FIG. 6 is a flowchart of an example method for managing surgical sutures in a robot-assisted surgical operation.

Referring to FIG. 6, an example method 500 for managing surgical sutures in a robot-assisted surgical operation is further described. The method 500 may begin at operation 502 in which a suture-carrying apparatus is inserted through a body opening into a body cavity defined with the human body. For example, in some cases the surgeon uses a standard laparoscopic instrument to pick up the apparatus and insert it to a body cavity through a body opening under direct visual guidance. In some embodiments, the body opening is created by a trocar, and the suture-carrying apparatus may be inserted through the trocar into the body cavity. Alternatively or in addition, a sleeve may be engaged with the body opening to maintain the body opening after the trocar is removed, and the suture-carrying apparatus may be inserted through the sleeve.

In some embodiments, the suture-carrying apparatus may have one or more surgical sutures engaged with a ridge of the apparatus before, or during, inserting the apparatus into the body cavity. Alternatively or in addition, surgical sutures can be provided to the apparatus after the apparatus is inserted and placed within the body cavity.

The suture-carrying apparatus may be made of one or more flexible materials such that a user may change its shape/size to make it suitable to pass through a small body wall opening (e.g., incision or hole) or through a tool (e.g., a trocar or a sleeve) engaged with the body hole. In some embodiments, the suture-carrying apparatus includes a base having one or more flexible wings that are easily deformable. For example, the wings may be rolled or folded to configure the apparatus into a lower, smaller, and/or narrower profile that is sized to pass through the body hole or the tool engaged with the body hole. To facilitate insertion of the apparatus though a body hole or a tool engaged with the body hole, in some embodiments, the apparatus may be grasped by one or more grasping devices of one or more robot arm assemblies while the apparatus is deformed in a smaller and/or narrower profile. In other embodiments, the apparatus is naturally deformed or flexed to fit through a body hole or the tool engaged with the body hole as the apparatus is delivered through the body hole or the tool using the grasping device of the robot arm assembly.

At operation 504, the suture-carrying apparatus that is positioned within the body cavity is then placed on or against a body structure within the body cavity, such as an organ or tissue surface. In some embodiments, the suture-carrying apparatus is first reconfigured to extend the wings, and then it is mounted to (or abutted against) the organ surface. In some embodiments, a suction cup effect may be generated when the apparatus is pushed against the body structure. In other embodiments, other techniques (e.g., the natural adhesion between the flexible silicon wings and a moist tissue surface) may be used to mount the apparatus to a desired body structure within the body cavity.

At operation 506, one or more robotic arm assemblies are controlled to remove a surgical suture from engagement with the suture-carrying apparatus, and use the surgical suture for an intended process such as stitching. In some embodiments, a robotic arm assembly is coupled to a surgical instrument, such as a grasping device, which can be used to engage and retrieve a surgical suture from the apparatus.

At operation 507, one or more robotic arm assemblies are controlled to return the surgical needles to the suture-carrying apparatus in preparation for removing the suture-carrying apparatus and surgical needles from the body cavity.

At operation 508, the suture-carrying apparatus and engaged surgical needles may be removed from the body cavity through the body hole. Such removal may happen in various situations, such as once a desired process is completed within the body cavity, when the apparatus needs to be refilled with additional surgical sutures outside the body cavity, or when the apparatus needs to be replaced with another suture-carrying apparatus. The suture-carrying apparatus may be removed directly through the body hole, or through the tool (e.g., trocar or sleeve) that is engaged with the body hole. For example, one or more robot arm assemblies may be controlled to grasp the apparatus and take it out from the body cavity through the body hole or the tool. As the suture-carrying apparatus is made of one or more flexible materials, the apparatus may be deformed into a smaller or narrower profile (e.g., rolled, folded, etc.) so that the apparatus easily passes through the body hole or the trocar or sleeve engaged with the body hole.

Figure 7:
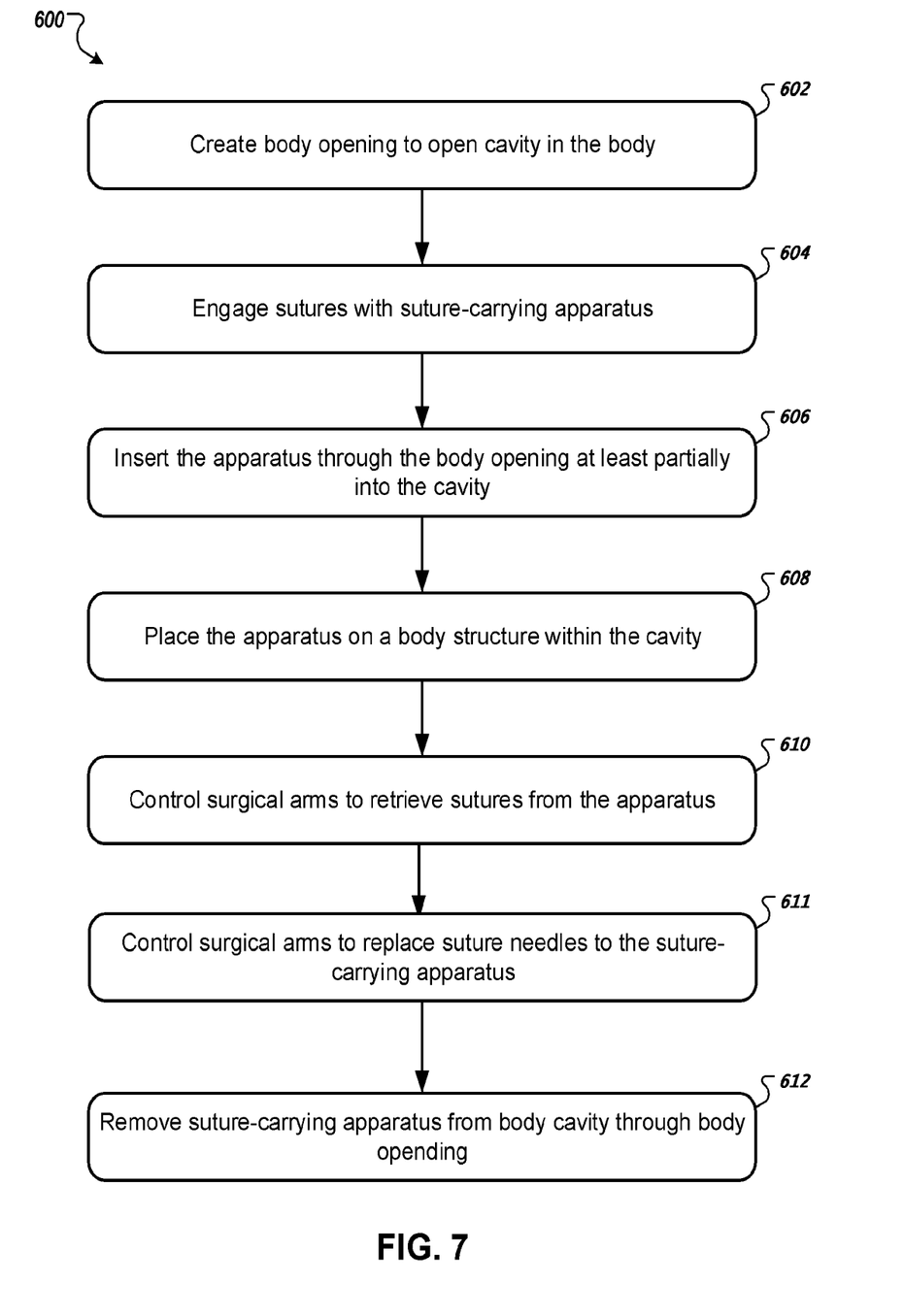
FIG. 7 is a flowchart of an example method for managing surgical sutures in a robot-assisted surgical operation.

Referring to FIG. 7, an example method 600 for managing surgical sutures in a robot-assisted surgical operation is described. The method 600 may begin with operation 602 of creating a body opening or hole on a body portion to open a body cavity defined with the a human body.

The method 600 may include operation 604 of engaging one or more surgical sutures with a suture-carrying apparatus (operation 604). The suture-carrying apparatus may be prepared with surgical sutures in various stages, such as before, during, or after inserting the suture-carrying apparatus into the body cavity. In some embodiments, surgical sutures may be engaged with a ridge of the apparatus while the apparatus includes a base configured to mount the ridge to a body structure. The base may include one or more flexible wings extending from a bottom of the ridge and at least partially around the ridge.

The method 600 may include operation 606 of inserting the suture-carrying apparatus through the body opening at least partially into the body cavity. The operation 606 may include deforming (e.g., rolling, folding, twisting, etc.) the suture-carrying apparatus to become a smaller and/or narrower profile to fit through the body opening that may or may not engage a tool, such as a trocar, a sleeve, or other devices for keeping the body opening open to certain size.

The method 600 may include operation 608 of placing the suture-carrying apparatus onto a body structure within the body cavity. In some embodiments, the operation 608 may include placing the flexible base of the apparatus onto an organ surface with suction pressure generated at the base when the base is pressed against the organ surface.

The method 600 may include operation 610 of controlling one or more robotic arm assemblies of a robot-assisted surgical system to retrieve one or more of the surgical sutures from the apparatus within the cavity. The operation 610 may include controlling a grasping device attached to a working end of a robotic arm assembly to move close to the apparatus and manipulate the grasping device to grasp one of the surgical sutures and remove it from the engagement with the apparatus.

At operation 611, one or more robotic arm assemblies are controlled to return the surgical needles to the suture-carrying apparatus in preparation for removing the suture-carrying apparatus and surgical needles from the body cavity.

The method 600 may include operation 612 of removing the suture-carrying apparatus from the body cavity through the body opening as necessary. The operation 612 may be performed when all desired procedures using surgical sutures have been completed and the body opening needs to be closed, when additional sutures need to be provided with the apparatus for further procedures, or when other sutures need to be provided with another suture-carrying apparatus that replaces the current suture-carrying apparatus in the body cavity. As the suture-carrying apparatus is made of one or more flexible materials, the suture-carrying apparatus may be deformed to fit through the body opening as the suture-carrying apparatus is taken out from the body cavity.

Figure 8:
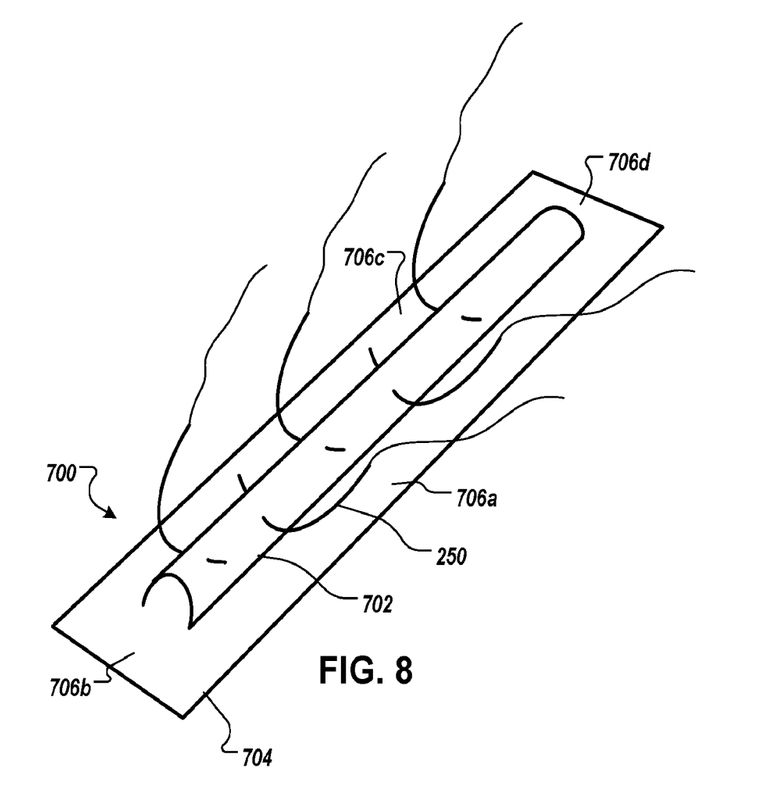
FIG. 8 is a perspective view of another example suture-carrying apparatus.
Figure 9:
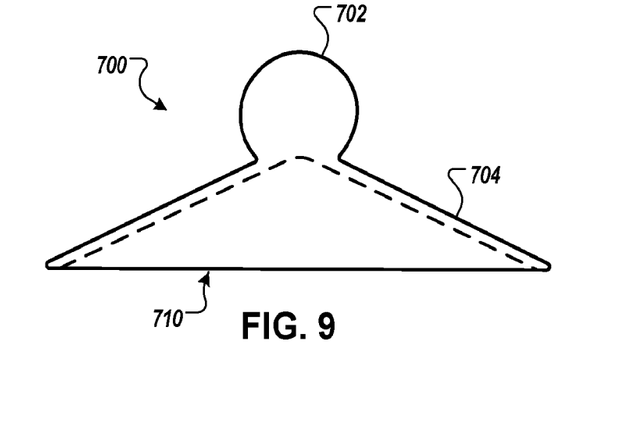
FIG. 9 is an end view of the suture-carrying apparatus of FIG. 8.

Referring to FIGS. 8 and 9, another example suture-carrying apparatus 700 is depicted. The suture-carrying apparatus 700 is configured to carry and manage surgical sutures 250 in robot-assisted surgical operations and may include a ridge 702 and a base 704. The ridge 702 may be formed as an elongate body (e.g., block, tube, cylinder, or other shapes) configured to removably engage and retain one or more surgical sutures 250.

The ridge 702 can be made of one or more flexible materials, such as silicon, and permit the surgical sutures to pierce and remain engaged with the ridge 702. In some implementations, the ridge 702 longitudinally extending along the base 704. As illustrated in FIG. 8, surgical sutures 250 can pass through the opposite side surfaces of the ridge 702 and engage with the ridge 702 for storage. In some embodiments, the material of the ridge 702 exhibits a higher durometer (harder) than the material of the base 704. For example, in some embodiments the ridge 702 is a hard silicone and the base 704 is a soft silicone.

The base 704 is configured to removably mount the apparatus 700 to a body structure, such as on a body skin or within a body cavity. The base 704 may be made of one or more flexible materials, such as silicon. In some implementations, the base 704 may include one or more flexible wings 706 that are attached to a bottom of the ridge 702. The wings 706 may be connected to the bottom of the ridge 702 and arranged at least partially around the ridge 702. In embodiments where the ridge 702 includes four edges at the bottom, the base 704 may include four wings 706a, 706b, 706c, and 706d connected at the edges of the bottom of the ridge 702, respectively.

In some embodiments, the wings 706a-d may be configured as a single integral piece that is attached to the bottom of the ridge 702 such that the wings 706a-d spread out from the bottom of the ridge 702. In some embodiments, the wings 706a-d may extend away from the ridge 702 and downwardly from the bottom of the ridge 702. In some embodiments, the wings 706a-d may be interconnected to one another (or formed as a single integral piece) around the ridge 702, thereby forming a recessed portion 710 (also referred to as a suction cup). The recessed portion 710 of the base 704 can create a suction cup effect when the base 704 is mounted to a surface of a body portion, such a body skin or an organ surface.

The wings 706a-d may be made of one or more flexible materials, such as silicon, and configured to flap (e.g., be limp or flaccid) relative to the ridge 702. As the wings 706a-d are flexible, the base 704 can deform in various configurations and result in a smaller profile for use by the apparatus 100 (FIGS. 1A and 1B).

Figure 10:
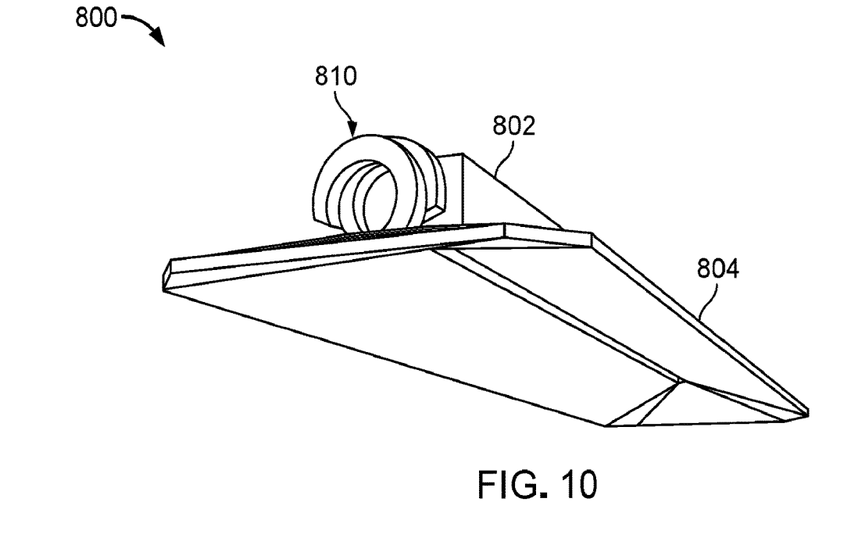
FIG. 10 is a perspective view of another example suture-carrying apparatus.
Figure 11:
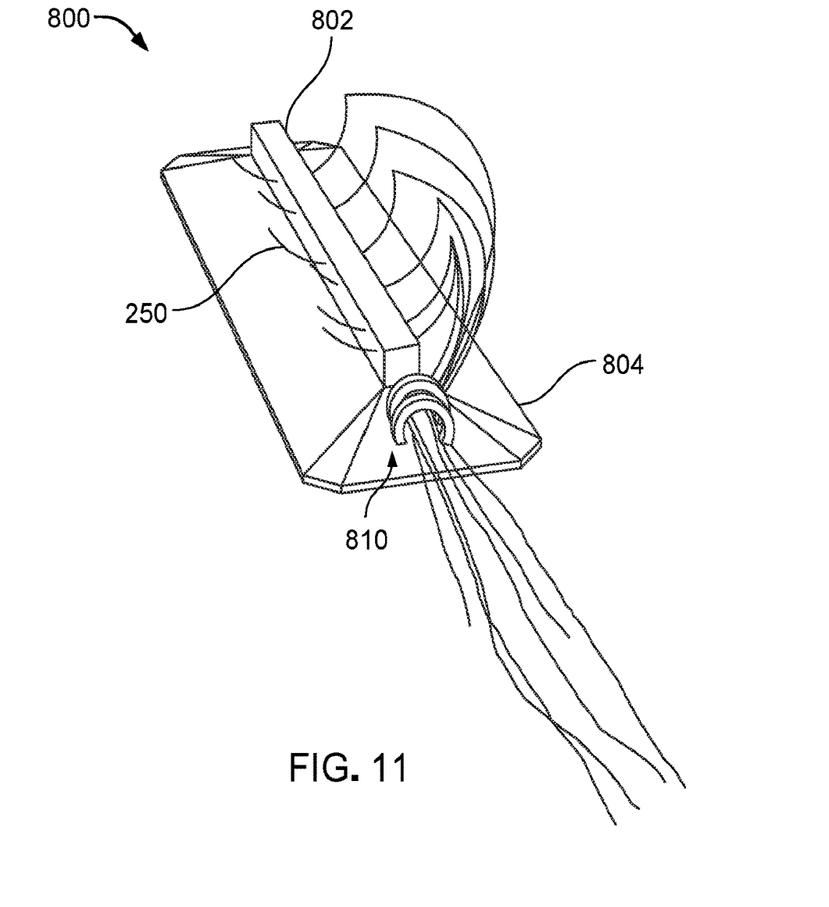
FIG. 11 is another perspective view of the suture-carrying apparatus of FIG. 10, with multiple sutures attached thereto.

FIGS. 10 and 11 depict an optional feature that can be included with any of the suture-carrying apparatuses described herein. That is, the example suture-carrying apparatus 800 includes a suture thread retaining structure 810. As shown in FIG. 11, the suture thread retaining structure 810 can be used to releasably contain the threads of the sutures 250 that are engaged with the ridge 802. This helps to organize the threads of the sutures 250 and prevent entanglement of the threads.

As depicted, in some embodiments the suture thread retaining structure 810 is attached to the base 804. There can be one (as shown), two, three, four or more of the suture thread retaining structures 810 included. In the depicted embodiment, the suture thread retaining structure 810 comprises two flexible C-shaped members that are attached to the base 804 at a single end of the respective C-shape. As shown, the two C-shaped members can be adjacent to each other such that a tunnel is defined through the thread retaining structure 810 (in which the threads of the sutures 250 are releasably detained). As shown, in some embodiments the ends of the C-shaped members that are attached to the base 804 can be on opposite sides of the C-shaped members. That arrangement provides good containment of the suture threads. Alternatively, in some embodiments the ends of the C-shaped members that are attached to the base 804 can be on the same sides of the C-shaped members.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. An apparatus for managing surgical sutures in a robot-assisted surgical operation, the apparatus comprising:
   an elongate ridge configured to be pierced by one or more surgical needles and to removably retain the one or more surgical needles that are pierced into the elongate ridge, wherein a length of the elongate ridge extends along two sides of the elongate ridge from a first end of the elongate ridge to a second end of the elongate ridge, wherein the first and second ends of the elongate ridge are spaced apart from each other at opposite ends of the elongate ridge, and wherein the length is greater than a height and a width of the elongate ridge; and
   a flexible base attached to the elongate ridge and configured to removably mount the elongate ridge to a body structure, the flexible base including:
      a first side wing having a trapezoidal shape that extends laterally outward and downward from a bottom of a first side of the two sides of the elongate ridge; and
      a second side wing having a trapezoidal shape that extends laterally outward and downward from a bottom of a second side of the two sides of the elongate ridge,
      wherein the first and second side wings define a concave bottom surface of the flexible base whereby the flexible base is a suction cup,
   wherein the apparatus is reconfigurable between: (i) a low-profile arrangement in which the first and second side wings are contracted toward the elongate ridge such that the apparatus can be passed through a trocar or body incision and (ii) an expanded arrangement in which the first and second side wings are extended away from the elongate ridge.

2. The apparatus of claim 1, further comprising a suture thread retaining structure attached to the flexible base, the suture thread retaining structure configured to releasably detain suture threads that are attached to the one or more surgical needles that are retained with the elongate ridge.

3. The apparatus of claim 2, wherein the suture thread retaining structure comprises two flexible members that each comprise: (i) an arcuate cross-sectional shape, (ii) a first end attached to the flexible base, and (iii) a second end that is spaced apart from the flexible base.

4. The apparatus of claim 3, wherein the two flexible members are attached adjacent to each other at a single end of the flexible base.

5. The apparatus of claim 4, wherein a first flexible member of the two flexible members extends from its first end to its second end along a clockwise direction, and wherein a second flexible member of the two flexible members extends from its first end to its second end along a counter-clockwise direction.

6. The apparatus of claim 1, wherein the flexible base further comprises:
   a first end wing extending outward and downward from a bottom of the first end of the elongate ridge; and
   a second end wing extending outward and downward from a bottom of the second end of the elongate ridge.

7. The apparatus of claim 6, wherein the first and second side wings are each longer than the first and second end wings.

8. The apparatus of claim 1, wherein the first and second side wings are configured to be softer and more flaccid relative to the elongate ridge.

9. The apparatus of claim 1, wherein the body structure includes an organ.

10. The apparatus of claim 1, wherein the flexible base includes a plurality of wings including at least the first side wing and the second side wing, the flexible base includes the same number of the plurality of wings as a number of bottom edges of the elongate ridge.

11. The apparatus of claim 1, wherein the apparatus is made of one or more flexible materials with identical flexibilities.

* * * * *